(12) United States Patent
De Meuter et al.

(10) Patent No.: US 7,108,886 B2
(45) Date of Patent: Sep. 19, 2006

(54) SUGAR-FREE HARD COATINGS PREPARED FROM LIQUID MIXTURES OF ERYTHRITOL AND SORBITOL

(75) Inventors: Pascale Adolphine Emilienne De Meuter, Vilvoorde (BE); Benjamin Christiane Robert Alexandre, Eppegem (BE)

(73) Assignee: Cerestar Holding B.V., La Sas van Gent (NL)

( * ) Notice: Subject to any disclaimer, the term of this patent is extended or adjusted under 35 U.S.C. 154(b) by 389 days.

(21) Appl. No.: 10/626,631

(22) Filed: Jul. 25, 2003

(65) Prior Publication Data
US 2005/0079245 A1    Apr. 14, 2005

Related U.S. Application Data

(62) Division of application No. 09/586,964, filed on Jun. 5, 2000.

(30) Foreign Application Priority Data
Jun. 3, 1999   (GB) ................................. 9912813.4

(51) Int. Cl.
A23L 1/236    (2006.01)
(52) U.S. Cl. ............................ 426/548; 426/3; 426/89; 426/302; 426/660

(58) Field of Classification Search ................ 426/3, 426/89, 103, 302, 303, 304, 307, 548, 658, 426/660
See application file for complete search history.

(56) References Cited

U.S. PATENT DOCUMENTS

| | | | |
|---|---|---|---|
| 4,127,677 A | 11/1978 | Fronczkowski et al. |
| 4,238,510 A | 12/1980 | Cherukuri et al. |
| 4,423,086 A | 12/1983 | Devos et al. |
| 5,536,511 A | 7/1996 | Yatka |
| 5,545,417 A | 8/1996 | Richey et al. |
| 5,571,547 A | 11/1996 | Serpelloni et al. |
| 5,980,955 A | 11/1999 | Greenberg et al. |
| 6,017,567 A | 1/2000 | Rosenplenter |

FOREIGN PATENT DOCUMENTS

| | | |
|---|---|---|
| EP | 0 813 817 | 12/1997 |
| WO | WO 95/07625 | 3/1995 |

*Primary Examiner*—Leslie Wong
(74) *Attorney, Agent, or Firm*—Fitch, Even, Tabin & Flannery

(57) ABSTRACT

The present invention discloses a sugar-free hard coating prepared from a liquid coating syrup comprising a mixture from sorbitol and erythritol. Coating with liquid mixtures of sorbitol and erythritol gives a crunchy hard coating, which is well adhered to the gum base. The invention also relates to products coated with the said compositions.

13 Claims, 4 Drawing Sheets

A = hard coating
B = adhesion of hard coating to core
C = core

A = hard coating
B = bad adhesion of hard coating to core
C = core

← A

A = hard coating

← A

A = hard coating

SUGAR-FREE HARD COATINGS PREPARED FROM LIQUID MIXTURES OF ERYTHRITOL AND SORBITOL

This is a divisional application of U.S. application Ser. No. 09/586,964, filed Jun. 5, 2000, the complete disclosure of which is incorporated herein by reference.

TECHNICAL FIELD

The present invention relates to a sugar-free hard coating prepared from a liquid coating syrup comprising a mixture from sorbitol and erythritol. The present invention relates to sugar-free hard coatings giving good adhesion to cores consisting of edible, chewable or pharmaceutical components. The invention also relates to products coated with the said compositions. The coatings based on the compositions of the present invention show good crispiness and/or crunchiness.

BACKGROUND OF THE INVENTION

Conventional panning procedures to prepare hard coatings generally work with sucrose, but recent advances in panning have allowed the use of other carbohydrate materials to be used in the place of sucrose. Sucrose proves to be detrimental for teeth and causes dental caries due to easy formation of acids. Therefore coatings are nowadays increasingly made of sugar-free compositions.

U.S. Pat. No. 4,127,677 describes a sugarless xylitol-coated chewing gum, which delivers an intense cooling effect and which has a pleasant smooth feel. However the cost of xylitol is quite high and partial replacement of xylitol in the coating would be an advantage.

To obtain good hard coatings, fast even crystallisation must occur during application and drying.

WO 95/07625 describes the advantages of at least partial replacement of xylitol with erythritol in chewing gum coating. In a specific example erythritol and xylitol are used together in a single layer, since both polyols are co-crystallised. Preferably the xylitol portion of the solids in the solution should be about 40% to about 80% xylitol, with the solids in the solution comprising about 20% to about 60% erythritol. However, example 6 demonstrates that the hard coating easily peels from the gum core and it has a slight sandpaper finish. This example demonstrates that application of polyol mixtures in hard coatings is very sensitive to the ratio of the polyols and depends on the kind of polyol applied. Furthermore, the appearance of the coating is sometimes affected by the crystallisation difficulties.

On the other hand sorbitol has been suggested as a substitute for sugar in sugarless preparations. However, it is common general knowledge that sorbitol can be used as an ingredient of the core but difficulties might arise to apply sorbitol in hard coatings, due to its hygroscopic nature. The major drawback of the use of sorbitol is that the resulting coating layers do not show the same crunchiness and crispiness as the conventional sucrose-based coatings.

U.S. Pat. No. 4,238,510 discloses a method for sorbitol coating wherein it is ensured that the sorbitol crystallises. By this method cycles are repeatedly carried out comprising a) application of a first coating syrup containing sorbitol, an adhesion or binder component and a film-forming agent, b) application of a dry dusting powder in the form of a mix comprising sorbitol in a powdered form, a moisture absorbing component, an anti-sticking component and a dispersing agent. It is believed that the crystalline powder acts as a seed crystal for the saturated sorbitol solution. However, the obtained result is not satisfactory since the coating layer is not evenly distributed, and rough surfaces are obtained, while the hard coating is not as crunchy as is obtained with normally employed sugars.

U.S. Pat. No. 4,423,086 describes that hard coatings based on sorbitol can be obtained when applying a coating syrup having a concentration of dry matter comprised between 60 to 85% by weight and the richness of the syrup in sorbitol being greater than 80%, preferably greater than 95%, and still more preferably greater than 99%. On the other hand the sorbitol based coatings are less expensive but lack the important cooling effect of the hard coatings based on xylitol which is giving the pleasant smooth feeling and which is especially desirable for the application of hard coatings of chewing gums. In this respect, sorbitol coatings are improved by the addition of other polyols, which have this important cooling effect.

However U.S. Pat. No. 5,536,511 mentions that it has been difficult in practice to use more than 5% sorbitol in a xylitol panning coating, and at these low levels, sorbitol acts as a crystallisation modifier. These coatings with limited amount of sorbitol lack the cost-effective advantage.

So far sorbitol based hard coatings contain either more than 80% sorbitol, preferably more than 99% sorbitol, or the hard coatings are based on mixtures of sorbitol with other polyols such as xylitol, but then the quantity of sorbitol is practically limited to 5%.

EP 0813817 discloses a process for coating cores with mixtures of sorbitol and other polyols, wherein the concentration of sorbitol is not limited to 5%. The applied process is different from the panning procedures, which are applying solely liquid coating syrups, and consequently the obtained products are different. The sorbitol syrup is applied to a rotating mass of cores and then at least one other polyol is added in a crystalline form. Preferably, the polyol is selected from the group consisting of Isomalt", xylitol, and erythritol. The crunchiness is at least comparable to that obtained with sucrose. However, the mentioned method requires the addition of the second polyol in crystalline form. Accordingly, a need exists in the market place for a cheap sugarless coating prepared from liquid mixtures of polyols, resulting in a crunchy hard coating, which is well adhered to the gum base.

SUMMARY OF THE INVENTION

The present invention relates to sugar-free hard-coated comestibles consisting of a hard coating and an edible, chewable and/or pharmaceutical core characterised in that at least one layer of the hard coating is comprising a mixture of sorbitol and erythritol wherein the dry substance of the mixture is comprising between 1% to 50% w/w erythritol.

The present invention relates to sugar-free hard-coated comestibles wherein the dry substance of the mixture comprises between 5% to 50% w/w erythritol, preferably between 5% to 45% w/w erythritol, more preferably between 20% to 45% w/w erythritol.

The present invention further relates to sugar-free hard-coated comestibles wherein the layer of the hard coating comprising a mixture of sorbitol and erythritol is effecting good adhesion to the core.

The present invention discloses sugar-free hard-coated comestibles wherein the layer of the hard coating is comprising binding agents, dispersing agents, film formers, colouring agents, and/or flavouring agents.

The present invention further relates to sugar-free hard-coated comestibles wherein the hard coating consists of from 1 to 100 layers.

The sugar-free coatings of the present invention are used for coating the cores selected from the group consisting of pharmaceutical tablets, chewing gum, confectionery products (such as candies), chocolate and nuts.

The present invention discloses hard-coated comestibles, which are coated by applying the rotating panning process. The process for preparing sugar-free hard-coated comestibles comprises the addition of a liquid coating syrup to the moving mass of the cores in a rotating pan characterised in that the liquid coating syrup is comprising a mixture of sorbitol and erythritol wherein the dry substance of the mixture is comprising between 1% to 50% w/w erythritol, and the application of the layers is repeated up to 100 times.

It shows the hard coating prepared with the liquid coating syrup of the mixture of 60% w/w sorbitol and 40% w/w erythritol.

It is clearly seen that the hard coating is very well adhered to the gum base.

Figure 2:
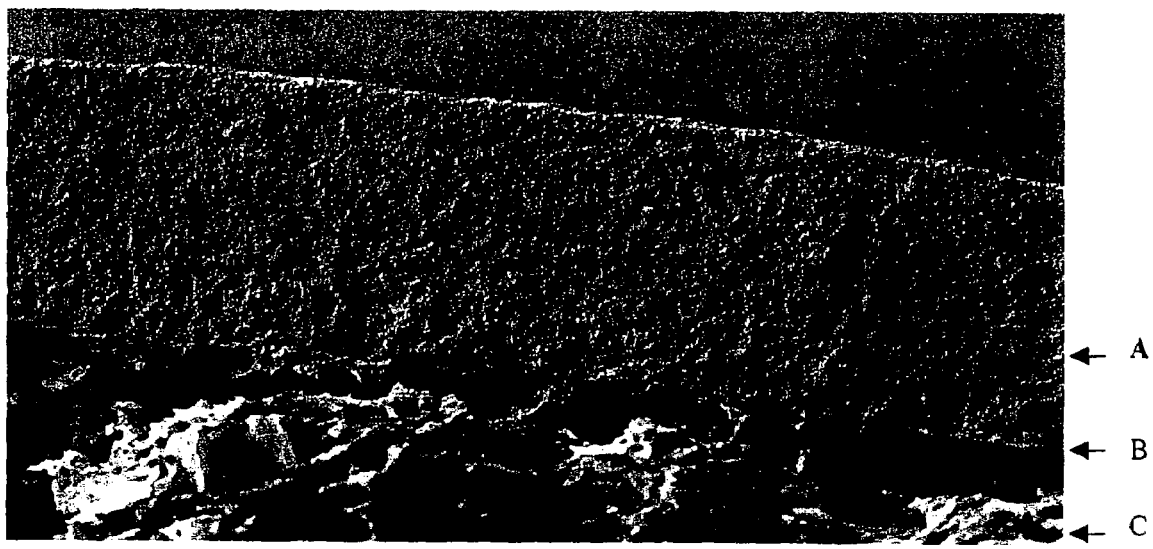

FIG. 2 is a scanning electron microscope picture, with magnification of 250×, measured at 10 kV, of the cross-section of a gold-coated sample.

It shows the hard coating prepared with the liquid coating syrup of the mixture of 40% w/w xylitol and 60% w/w erythritol.

It is clearly seen that the hard coating is less good adhered to the gum base.

Figure 3:
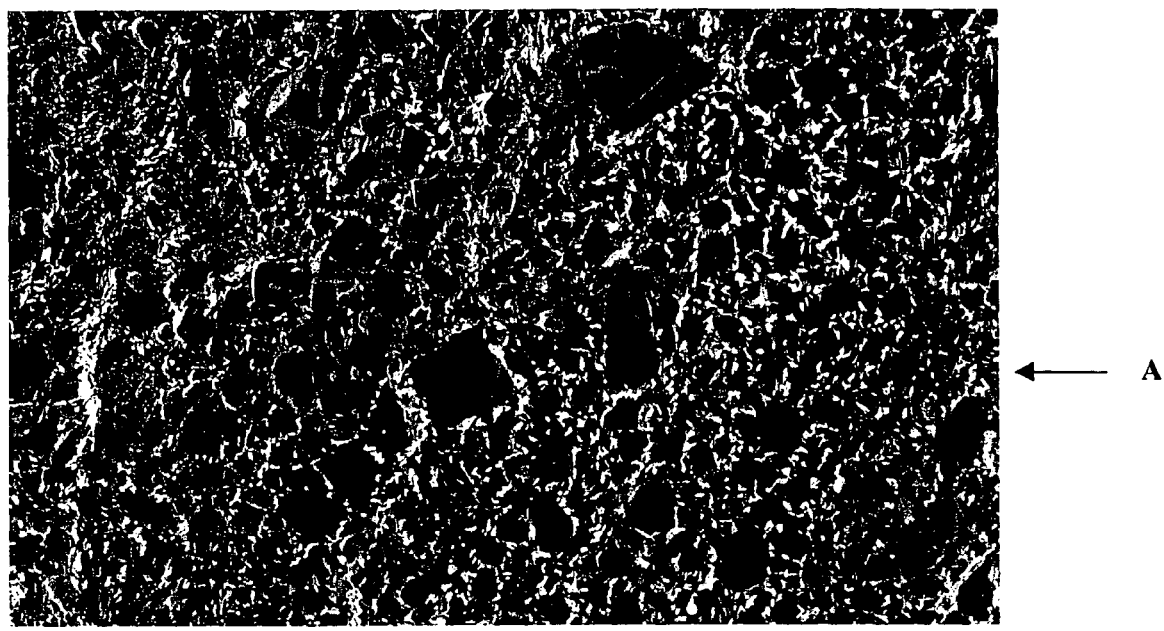

FIG. 3 is a scanning electron microscope picture, with magnification of 3000×, measured at 10 kV, of the cross-section of a gold-coated sample.

It shows that the hard coating, prepared with the liquid coating syrup of the mixture of 60% w/w (based on dry substance) sorbitol and 40% w/w erythritol, is homogeneous and there is a uniform distribution of the erythritol and sorbitol crystals.

Figure 4:
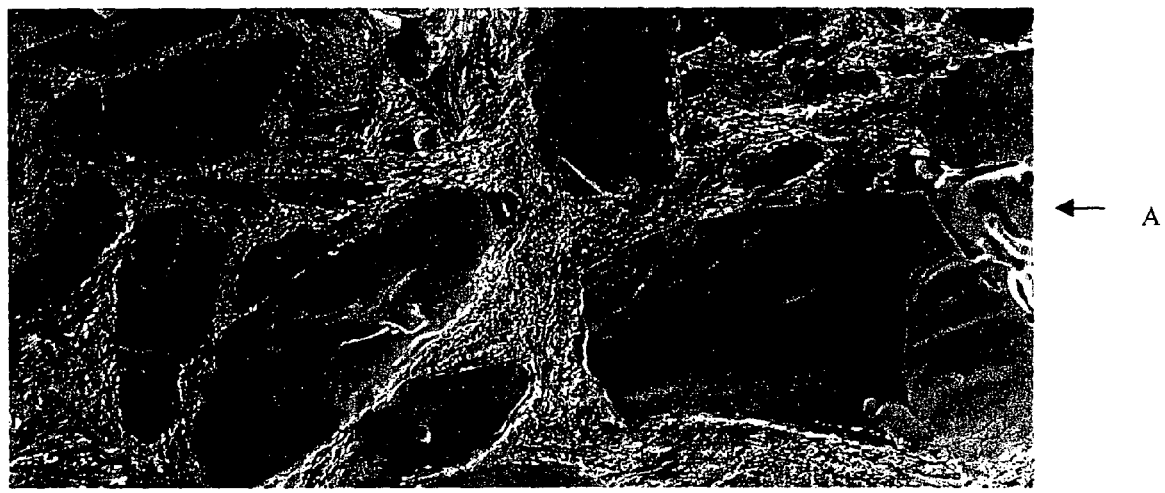

FIG. 4 a scanning electron microscope picture, with magnification of 3000×, measured at 10 kV, of the cross-section of a gold-coated sample.

It shows that the hard coating, prepared according to the process described in EP 0813817, is heterogeneous and it is consisting of big erythritol crystals in the sorbitol matrix.

DETAILED DESCRIPTION OF THE INVENTION

The present invention relates to sugar-free hard-coated comestibles consisting of a hard coating and an edible, chewable and/or pharmaceutical core characterised in that at least one layer of the hard coating is comprising a mixture of sorbitol and erythritol and wherein the dry substance of the mixture is comprising between 1% to 50% w/w erythritol.

The present invention relates to sugar-free hard-coated comestibles wherein the dry substance of the mixture comprises between 5% to 50% w/w erythritol, preferably between 5% to 45% w/w, more preferably between 20% to 45% w/w erythritol.

The present invention discloses liquid coating syrups comprising mixtures of sorbitol and erythritol, wherein the dry substance of the mixture is comprising between 1 to 50% w/w erythritol, preferably between 5% to 45% w/w, more preferably between 20% and 45% w/w erythritol. These coating syrups give rise to crispy and/or crunchy hard coatings with a uniform smooth surface and with good adhesion to the core. At least one layer of the hard coating is comprising a mixture of sorbitol and erythritol, and this layer is effecting the good adhesion to the core.

Sorbitol is defined as the hydrogenated product resulting from dextrose or glucose syrups that are containing higher polyols, and sorbitol is applied in solid or liquid form.

Erythritol may be obtained by a fermentative process or it may also be obtained from a chemical process such as the conversion of dialdehyde starch, tartaric esters or tartaric acid, and it gives the same cooling effect as xylitol. Moreover erythritol does not contribute to dental caries, does not significantly contribute to calories and does not cause gastric distress like some other polyols. Erythritol is available as non-hygroscopic crystalline powder.

The present invention discloses the preparation of hard-coated comestibles, which consists of a hard coating and an edible, chewable and/or pharmaceutical core and wherein the hard coating is adhered well to the core. At least one layer is prepared from the liquid mixture of sorbitol and erythritol to obtain the good adhesion to the core. This layer may be the first layer which is in direct contact with the core, and/or it may be a layer which is close enough to the core for effecting good adhesion to the core. The other layers may consist of single polyols. Preferably the sugar-free coatings of the present invention are used for coating pharmaceutical tablets, chewing gum, confectionery products (such as candies), chocolate and nuts.

When the present invention is applied for hard coating of chewing gum, any conventional chewing gum centre (core) may be used. Preferably the centre is sugar-free and constitutes from about 35 to about 65% of the chewing gum product.

Liquid coating syrups devoid of any binding or film forming agent, but consisting of a mixture of sorbitol and erythritol wherein the dry substance of sorbitol in the mixture is lower than 50% w/w, give rise to rough irregular surfaces. Mixtures of sorbitol and erythritol, wherein the dry substance of sorbitol in the mixture is lower than 50% w/w, may however give rise to smooth regular surfaces when applying liquid coating syrups that contain additional ingredients, such as binding agents, or film forming agents.

The best results are obtained with liquid coating syrups comprising mixtures wherein the dry substance of the mixture is consisting of 60% w/w sorbitol and 40% w/w erythritol.

The composition of the liquid coating syrup is not limited to the mixture of sorbitol and erythritol, but it may contain additionally some other ingredients such as artificial sweeteners, dispersing agents, colouring agents, film formers, binding agents, and/or flavouring agents.

The coating syrup is initially present as a liquid syrup which contains from about 30% to 80% or 85% dry substance consisting of the coating ingredients previously described herein, and from about 15% or 20% to about 70% of a solvent such as water.

In general, the hard coating process is carried out in a rotating pan. Cores to be coated are placed into the rotating pan to form a moving mass. The applied liquid coating syrup is comprising a mixture of sorbitol and erythritol wherein the dry substance of the mixture is consisting of between 1% to 50% w/w erythritol. This material or syrup, which will form the hard coating is applied or distributed over the cores and drying is performed with air. The drying air is in the temperature range of from about 15 to 45° C. and a moisture content of at most 50% relative humidity is applied. Each component of the coating on the core may be applied in a single hard layer or in a plurality of hard layers. In general a plurality of layers is obtained by applying single coats, allowing the layers to dry, and then repeating the process. Any number of the coats may be applied to the core. Coatings of from 1 to 100 layers are easily obtained, preferably the number of layers is between 1 and 40. The optimal amount of layers will depend on the desired application and can be determined experimentally.

The effectiveness of the hard coating, prepared according to the present invention is compared to the hard coating prepared from a liquid coating syrup containing erythritol and xylitol (example 3). The hard coating prepared from the liquid mixture of sorbitol and erythritol is superior in quality, since the adhesion to the gum core is much better.

Furthermore, in a comparative example the hard coating of the current invention is compared with the hard coating prepared according to the process as it is described in EP 0813817. The scanning electron microscope pictures (FIGS. 3 and 4) clearly demonstrate that the different processes give rise to different products.

The present invention is illustrated by way of the following examples.

EXAMPLE 1

Panning Conditions

To prepare the liquid mixture of sorbitol/erythritol 60/40 (trial 1), 11.2 kg erythritol (C☆Eridex 16952) were mixed with 16.8 kg sorbitol (C☆Sorbidex P16616) and 12 kg water. The resulting mixture was stored at 60° C.

The coating was performed in a pilot Driacoater.

50 kg cores, wherein the weight of uncoated centres was 0.9 g each, were rotating at 8 rpm and 0.6 kg of coating syrup was applied each time. The drying step was carried out by blowing air in at the bottom of the drying pan at 24° C.

Further applied panning conditions are mentioned in Table 1.

TABLE 1

| Conditions | Phase 2 | Phase 3 | Phase 4 | Phase 5 | Phase 6 | Phase 7 | Phase 8 |
| --- | --- | --- | --- | --- | --- | --- | --- |
| Drying T(° C.) | 24 | 24 | 24 | 24 | 24 | 24 | 24 |
| Total dosing (kg) | 4.2 | 0.6 | 0.6 | 21.6 | 2.4 | 0.3 | 0.0 |
| # kg/dosage | 0.6 | 0.6 | 0.6 | 0.6 | 0.6 | 0.6 | 0.0 |
| Smoothing t (sec) | 25 | 60 | 25 | 60 | 240 | 300 | 300 |
| Drying t (sec) | 300 | 300 | 300 | 400 | 200 | 600 | 900 |

Figure 1:
FIG. 1 is a scanning electron microscope picture, with magnification of 250×, measured at 10 kV, of the cross-section of a gold-coated sample.

FIG. 1 shows clearly that the hard coating is well adhered to the core.

FIG. 3 (magnification of 3000) shows that the hard coating is homogeneous and there is a uniform distribution.

EXAMPLE 2

Liquid mixtures with other ratios of sorbitol/erythritol were prepared. About 40 kg of total liquid mixture was prepared and each time 50 kg cores, wherein the weight of uncoated centres was 0.9 g each, were rotated in a pilot Driacoater at 8 rpm.

The other applied panning conditions are mentioned in Table 1.

The composition of the liquid mixture of sorbitol (S) and erythritol (E) for the coating syrup, its storing temperature and the resulting properties of the hard coating are mentioned in Table 2.

The coating syrups were devoid of binding, dispersing or film forming agents and the resulting hard coatings were compared to the hard coating prepared in trial 1 (example 1).

TABLE 2

| Trial | Composition: weight ratio sorbitol(S)/ Erythritol (E), based on dry substance of mixture | Dry substance of coating syrup (%) | Temperature (° C.) of coating solution | Physicochemical-Organoleptic Evaluation |
| --- | --- | --- | --- | --- |
| 2 | S/E 30/70 | 70 | 65 | Rough surface, powdery |
| 3 | S/E 40/60 | 70 | 65 | Rough surface |
| 1 | S/E 60/40 | 70 | 60 | Smooth transparent surface, crunchy coating, cooling effect |

TABLE 2-continued

| Trial | Composition: weight ratio sorbitol(S)/ Erythritol (E), based on dry substance of mixture | Dry substance of coating syrup (%) | Temperature (° C.) of coating solution | Physicochemical-Organoleptic Evaluation |
|---|---|---|---|---|
| 4 | S/E 80/20 | 70 | 50 | Smooth transparent surface, crunchy coating, cooling effect |

EXAMPLE 3

A liquid mixture of erythritol and xylitol was prepared from 11.2 kg xylitol and 16.8 kg erythritol, 2 kg gelatine (33%) and 11.2 kg water. Everything was mixed and stored at 65° C.

A pilot Driacoater was filled with 50 kg cores, wherein the weight of uncoated centres was 0.9 g each, and the liquid mixture was applied while rotating at 8 rpm.

Further applied panning conditions are mentioned in Table 3.

TABLE 3

| Conditions | Phase 2 | Phase 3 | Phase 4 | Phase 5 | Phase 6 | Phase 7 |
|---|---|---|---|---|---|---|
| Drying T(° C.) | 24 | 24 | 24 | 24 | 24 | 24 |
| Total dosing (kg) | 0.6 | 0.6 | 2.4 | 24 | 1.2 | 0.0 |
| # kg/dosage | 0.3 | 0.6 | 0.6 | 0.8 | 0.6 | 0.0 |
| Smoothing t (sec) | 45 | 45 | 30 | 20 | 20 | 500 |
| Drying t (sec) | 250 | 300 | 275 | 350 | 275 | 500 |

The obtained results are displayed in Table 4.

TABLE 4

| Trial | Mixture | Ratio | Temperature (° C.) | Dry substance (%) | % gelatine | Evaluation |
|---|---|---|---|---|---|---|
| 1 | S/E | 60/40 | 75 | 70 | No addition | Crunchy |
| 5 | X/E | 40/60 | 65 | 70 | 1% | Bad adhesion |

FIG. 2 corresponds to the hard coating prepared in trial 5. It is clearly demonstrated that the hard coating is less good adhered to the core. This is in clear contrast to the good adhesion of the hard coating prepared according to trial 1, which is shown in FIG. 1.

FIG. 3 corresponds to the hard coating prepared in trial 1, but a magnification of 3000 is applied. It shows that the hard coating, prepared with the liquid coating syrup of the mixture of 60% w/w (based on dry substance of the mixture) sorbitol and 40% w/w erythritol, is homogeneous and there is a uniform distribution.

COMPARATIVE EXAMPLE

The process as it is described in EP 0813817 was repeated.

The coating solution was a sorbitol syrup with dry substance of 70% and a sorbitol-content of 97%. The syrup was applied to the cores at room temperature (20-25° C.).

2 kg cores were in a rotating pan (speed 20 rpm, diameter 0.5m, velocity at outer circumference 1 m/s). For the first ten layers 10 ml of sorbitol syrup was added. From layer twenty the amount was increased to 25 ml and from layer 37 it was further increased to 35 ml. Every fifth layer 1 min. after the addition of the sorbitol solution 0.57% (based on the weight of the centres) of C☆Eridex was added as a solid material.

The coating process was stopped after 40 layers.

FIG. 4 corresponds to the hard coating prepared according to this process. The hard coating is heterogeneous and it is consisting of big erythritol crystals in the sorbitol matrix. This is completely different from the hard coating prepared according to the current invention and displayed in FIG. 3.

The invention claimed is:

1. A process for preparing sugar-free hard-coated comestibles having a hard coating on an edible, chewable and/or pharmaceutical core, comprising the addition of a liquid coating syrup to a moving mass of cores for said comestibles in a rotating pan and obtaining a plurality of said sugar-free hard-coated comestibles having a hard coating on an edible, chewable and/or pharmaceutical core wherein at least one layer of the hard coating is directly in contact with the core, wherein the liquid coating syrup comprises a liquid mixture of sorbitol and erythritol wherein the dry substance of the liquid mixture comprises 60% w/w erythritol and 40% w/w sorbitol.

2. A process for preparing a sugar-free hard-coated comestible according to claim 1, wherein the application of the layers is repeated up to 100 times.

3. A process for preparing the sugar-free hard-coated comestible according to claim 1, wherein said moving mass of cores comprises edible, chewable and/or pharmaceutical cores.

4. A process for preparing the sugar-free hard-coated comestible according to claim 1, wherein the hard coating consists of from 1 to 100 layers.

5. A process for preparing the sugar-free hard-coated comestible according to claim 1, wherein said mixture comprises at least 5% w/w erythritol.

6. A process for preparing sugar-free hard-coated comestibles according to claim 1, wherein the core is selected from the group consisting of pharmaceutical tablets, chewing gum, confectionery product, chocolate and nut.

7. A process for preparing sugar-free hard-coated according to claim 1, wherein said hard coating has a smooth, regular surface.

8. A process for preparing sugar-free hard-coated comestibles according to claim 1, wherein said sugar-free hard-coated comestible has a pharmaceutical core.

9. A process for preparing sugar-free hard-coated comestibles according to claim 1, wherein said hard coating comprises at least one of binding agent, dispersing agent, film former, coloring agent or flavoring agent.

10. A process for preparing sugar-free hard-coated comestibles according to claim 1, wherein the hard coating consists of from 1 to 100 layers at least one of which comprises said mixture.

11. A process for preparing a sugar-free hard-coated comestible according to claim 1, wherein said at least one layer is a first formed on said core, and additional layers in said hard coating are formed from a member selected from the group consisting of said liquid mixture and single polyols.

12. A process for preparing a sugar-free hard-coated comestible according to claim 1, wherein said liquid syrup or said liquid mixture contains at least one ingredient selected from the group consisting of artificial sweeteners, dispersing agents, coloring agents, film formers, binding agents and flavoring agents.

13. A process for producing a sugar-free hard-coated comestible having a hard coating comprised of 1 to 100 layers and an edible, chewable and/or pharmaceutical core wherein a layer of the hard coating is in direct contact with said core and said layer is essentially homogeneous, said process comprising the steps of preparing a liquid mixture comprising a mixture of sorbitol and erythritol wherein the dry substance of the mixture comprises between 1% to 50% w/w erythritol, wherein said liquid mixture is for forming at least the layer of said hard coating that is in direct contact with said core; adding said liquid mixture to a rotating mass of cores to obtain coated cores; and obtaining a plurality of said sugar-free hard-coated comestibles.

* * * * *